United States Patent
Bergsma et al.

(12)

(10) Patent No.: US 6,287,801 B1
(45) Date of Patent: Sep. 11, 2001

(54) NUCLEIC ACIDS ENCODING THE G-PROTEIN COUPLED RECEPTOR HNFDS78

(75) Inventors: Derk Bergsma, Berwyn; Nabil Elshourbagy, West Chester; Henry Sarau, Harleysville, all of PA (US); Steven Ruben, Olney, MD (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 08/681,192

(22) Filed: Jul. 22, 1996

(51) Int. Cl.[7] .......................... C12N 15/12; C12N 15/63; C12N 15/85
(52) U.S. Cl. .................. 435/69.1; 435/325; 435/320.1; 435/252.3; 536/23.1; 536/23.5
(58) Field of Search .................. 536/23.1, 23.5; 435/69.1, 325, 320.1, 252.3

(56) References Cited

FOREIGN PATENT DOCUMENTS

9604388 * 2/1996 (WO).

OTHER PUBLICATIONS

Rudinger, In "Peptide Hormones" (Jun. 1976) ed. J.A. Parsons, University Park Press, Baltimore, pp 1–7.*
Devi et al., "Biological Activities of the β–Chemokine TCA3 on Neutrophils and Macrophages," The Jouranal of Immunology, 154: 5376–5383 (1995).
Bischoff et al., "RANTES and related chemokines activate human basophil granulocytes through different G protein––coupled receptors," Eur. J. Immunol. 23: 761–767 (1993).
Ben–Baruch, A. et al., "Monocyte Chemotactic Protein–3 (MCP3) Interacts with Multiple Leukocyte Receptors", J. Biol. Chem., 1995, 270:22123–22128.
Combadiere, C., et al., "Cloning and functional expression of CC CKR5, a human monocyte CC chemokine receptor selective for MIP–1α, and MIP–1β, and RANTES", J. Leuk. Biol., 1996, 60:147–152.
Power, C.A. et al., "Molecular Cloning and Functional Expression of a Novel CC Chemokine Receptor cDNA from a Human Basophilic Cell Line", J. Biol. Chem., 1995, 270(33):19495–19500.
Raport, C.J. et al., "Molecular Cloning and Functional Characterization of a Novel Human CC Chemokine Receptor (CCR5) for RANTES, MIP–1β and MIP–1α", J. Biol. Chem., 1996, 271(29):17161–17166.
Samson, M. et al., "Molecular Cloning and Functional Expression of a New Human CC–Chemokine Receptor Gene", Biochem., 1996, 35:3362–3367.

* cited by examiner

Primary Examiner—Gary L. Kunz
Assistant Examiner—Robert C. Hayes
(74) Attorney, Agent, or Firm—William T. Han; Ratner & Prestia; William T. King

(57) ABSTRACT

Human G-Protein Coupled Receptor HNFDS78 polypeptides and DNA (RNA) encoding such G-Protein Coupled Receptor HNFDS78 and a procedure for producing such polypeptides by recombinant techniques is disclosed. Also disclosed are methods for utilizing such G-Protein Coupled Receptor HNFDS78 for the treatment of diseases, such as, atherosclerosis, inflammatory disease, and infectious disease. Antagonists against such G-Protein Coupled Receptor HNFDS78 and their use as a therapeutic to treat disease are also disclosed. Also disclosed are diagnostic assays for detecting diseases related to mutations in the nucleic acid sequences and altered concentrations of the polypeptides. Also disclosed are diagnostic assays for detecting mutations in the polynucleotides encoding G-protein coupled receptors and for detecting altered levels of the polypeptide in a host.

13 Claims, 3 Drawing Sheets

G-Protein Coupled Receptor HNFDS78 cDNA Sequence and Predicted Amino Acid Sequence (A)  cDNA [SEQ ID NO:1]

```
   1  GNNNNGGGAG TCTATATAAG CAGAGCTGGG TACGTGAACC GTCAGATCGC
  51  CTGGAGACGC CATCGAATTC TGAAGATGGC CAATTACACG CTGGCACCAG
 101  AGGATGAATA TGATGTCCTC ATAGAAGGTG AACTGGAGAG CGATGAGGCA
 151  GAGCAATGTG ACAAGTATGA CGCCCAGGCA CTCTCAGCCC AGCTGGTGCC
 201  ATCACTCTGC TCTGCTGTGT TTGTGATCGG TGTCCTGGAC AATCTCCTGG
 251  TTGTGCTTAT CCTGGTAAAA TATAAAGGAC TCAAACGCGT GGAAAATATC
 301  TATCTTCTAA ACTTGGCAGT TTCTAACTTG TGTTTCTTGC TTACCCTGCC
 351  CTTCTGGGCT CATGCTGGGG GCGATCCCAT GTGTAAAATT CTCATTGGAC
 401  TGTACTTCGT GGGCCTGTAC AGTGAGACAT TTTTCAATTG CCTTCTGACT
 451  GTGCAAAGGT ACCTAgTGTT TTTGCACAAG GGCAACTTTT TCTCAGCCAG
 501  GAGGAGGGTG CCCTGTGGCA TCATTACAAG TGTCCTGGCA TGGGTAACAG
 551  CCATTCTGGC CACTTTGCCT GAATTCGTGG TTTATAAACC TCAGATGGAA
 601  GACCAGAAAT ACAAGTGTGC ATTTAGCAGA ACTCCCTTCC TGCCAGCTGA
 651  TGAGACATTC TGGAAGCATT TTCTGACTTT AAAAATGAAC ATTTCGGTTC
 701  TTGTCCTCCC CCTATTTATT TTTACATTTC TCTATGTGCA AATGAGAAAA
 751  ACACTAAGGT TCAGGGAGCA GAGGTATAGC CTTTTCAAGC TTGTTTTTGC
 801  CATAATGGTA GTCTTCCTTC TGATGTGGGC GCCCTACAAT ATTGCATTTT
 851  TCCTGTCCAC TTTCAAAGAA CACTTCTCCC TGAGTGACTG CAAGAGCAGC
 901  TACAATCTGG ACAAAAGTGT TCACATCACT AAACTCATCG CCACCACCCA
 951  CTGCTGCATC AACCCTCTCC TGTATGCGTT TCTTGATGGG ACATTTAGCA
1001  AATACCTCTG CCGCTGTTTC ATCTGCGTA GTAACACCCC ACTTCAACCC
```

Fig. 1A (B) Predicted Amino Acid Sequence [SEQ ID NO:2]

```
  1  MANYTLAPED EYDVLIEGEL ESDEAEQCDK YDAQALSAQL VPSLCSAVFV
 51  IGVLDNLLVV LILVKYKGLK RVENIYLLNL AVSNLCFLLT LPFWAHAGGD
101  PMCKILIGLY FVGLYSETFF NCLLTVQRYL VFLHKGNFFS ARRRVPCGII
151  TSVLAWVTAI LATLPEFVVY KPQMEDQKYK CAFSRTPFLP ADETFWKHFL
201  TLKMNISVLV LPLFIFTFLY VQMRKTLRFR EQRYSLFKLV FAIMVVFLLM
251  WAPYNIAFFL STFKEHFSLS DCKSSYNLDK SVHITKLIAT THCCINPLLY
301  AFLDGTFSKY LCRCFHLRSN TPLQPRGQSA QGTSREEPDH STEV
```

Fig. 1B cDNA Sequence and Predicted Amino Acid Sequence of Chemokine CKβ-8

(A) cDNA [SEQ ID NO:5]

```
  1 ATGAAGGTCTCCGTGGCTGCCCTCTCCTGCCTCATGCTTGTTACTGCCCTTGGATCCCAG   60
    M  K  V  S  V  A  A  L  S  C  L  M  L  V  T  A  L  G  S  Q

61 GCCCGGGTCACAAAAGATGCAGAGACAGAGTTCATGATGTCAAAGCTTCCATTGGAAAAT  120
    A  R  V  T  K  D  A  E  T  E  F  M  M  S  K  L  P  L  E  N

121 CCAGTACTTCTGGACAGATTCCATGCTACTAGTGCTGACTGCTGCATCTCCTACACCCCA  180
    P  V  L  L  D  R  F  H  A  T  S  A  D  C  C  I  S  Y  T  P

181 CGAAGCATCCCGTGTTCACTCCTGGAGAGTTACTTTGAAACGAACAGCGAGTGCTCCAAG  240
    R  S  I  P  C  S  L  L  E  S  Y  F  E  T  N  S  E  C  S  K

241 CCGGGTGTCATCTTCCTCACCAAGAAGGGGCGACGTTTCTGTGCCAACCCCAGTGATAAG  300
    P  G  V  I  F  L  T  K  K  G  R  R  F  C  A  N  P  S  D  K

301 CAAGTTCAGGTTTGCATGAGAATGCTGAAGCTGGACACACGGATCAAGACCAGGAAGAAT  360
    Q  V  Q  V  C  M  R  M  L  K  L  D  T  R  I  K  T  R  K  N

361 TGA 363
    *
```

Fig. 2A (B) Deduced amino acid sequence [SEQ ID NO:6]

MKVSVAALSCLMLVTALGSQARVTKDAETEFMMSKLPLENPVLLDRF

HATSADCCISYTPRSIPCSLLESYFETNSECSKPGVIFLTKKGRRFCANPSDK

QVQVCMRMLKLDTRIKTRKN

Fig. 2B

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1050 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

-continued

```
GNNNNGGGAG TCTATATAAG CAGAGCTGGG TACGTGAACC GTCAGATCGC CTGGAGACGC      60
CATCGAATTC TGAAGATGGC CAATTACACG CTGGCACCAG AGGATGAATA TGATGTCCTC     120
ATAGAAGGTG AACTGGAGAG CGATGAGGCA GAGCAATGTG ACAAGTATGA CGCCCAGGCA     180
CTCTCAGCCC AGCTGGTGCC ATCACTCTGC TCTGCTGTGT TTGTGATCGG TGTCCTGGAC     240
AATCTCCTGG TTGTGCTTAT CCTGGTAAAA TATAAAGGAC TCAAACGCGT GGAAAATATC     300
TATCTTCTAA ACTTGGCAGT TTCTAACTTG TGTTTCTTGC TTACCCTGCC CTTCTGGGCT     360
CATGCTGGGG GCGATCCCAT GTGTAAAATT CTCATTGGAC TGTACTTCGT GGGCCTGTAC     420
AGTGAGACAT TTTTCAATTG CCTTCTGACT GTGCAAAGGT ACCTAGTGTT TTTGCACAAG     480
GGCAACTTTT TCTCAGCCAG GAGGAGGGTG CCCTGTGGCA TCATTACAAG TGTCCTGGCA     540
TGGGTAACAG CCATTCTGGC CACTTTGCCT GAATTCGTGG TTTATAAACC TCAGATGGAA     600
GACCAGAAAT ACAAGTGTGC ATTTAGCAGA ACTCCCTTCC TGCCAGCTGA TGAGACATTC     660
TGGAAGCATT TTCTGACTTT AAAAATGAAC ATTTCGGTTC TTGTCCTCCC CCTATTTATT     720
TTTACATTTC TCTATGTGCA AATGAGAAAA ACACTAAGGT TCAGGGAGCA GAGGTATAGC     780
CTTTTCAAGC TTGTTTTTGC CATAATGGTA GTCTTCCTTC TGATGTGGGC GCCCTACAAT     840
ATTGCATTTT TCCTGTCCAC TTTCAAAGAA CACTTCTCCC TGAGTGACTG CAAGAGCAGC     900
TACAATCTGG ACAAAAGTGT TCACATCACT AAACTCATCG CCACCACCCA CTGCTGCATC     960
AACCCTCTCC TGTATGCGTT TCTTGATGGG ACATTTAGCA AATACCTCTG CCGCTGTTTC    1020
CATCTGCGTA GTAACACCCC ACTTCAACCC                                    1050
```

(2) INFORMATION FOR SEQ ID NO:2:

(i) SEQUENCE CHARACTERISTICS:
        (A) LENGTH: 344 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:2:

```
Met Ala Asn Tyr Thr Leu Ala Pro Glu Asp Glu Tyr Asp Val Leu Ile
  1               5                  10                  15

Glu Gly Glu Leu Glu Ser Asp Glu Ala Glu Gln Cys Asp Lys Tyr Asp
             20                  25                  30

Ala Gln Ala Leu Ser Ala Gln Leu Val Pro Ser Leu Cys Ser Ala Val
         35                  40                  45

Phe Val Ile Gly Val Leu Asp Asn Leu Val Val Leu Ile Leu Val
     50                  55                  60

Lys Tyr Lys Gly Leu Lys Arg Val Glu Asn Ile Tyr Leu Leu Asn Leu
 65                  70                  75                  80

Ala Val Ser Asn Leu Cys Phe Leu Leu Thr Leu Pro Phe Trp Ala His
                 85                  90                  95

Ala Gly Gly Asp Pro Met Cys Lys Ile Leu Ile Gly Leu Tyr Phe Val
            100                 105                 110
```

```
Gly Leu Tyr Ser Glu Thr Phe Phe Asn Cys Leu Leu Thr Val Gln Arg
            115                 120                 125

Tyr Leu Val Phe Leu His Lys Gly Asn Phe Phe Ser Ala Arg Arg Arg
            130                 135                 140

Val Pro Cys Gly Ile Ile Thr Ser Val Leu Ala Trp Val Thr Ala Ile
145                 150                 155                 160

Leu Ala Thr Leu Pro Glu Phe Val Val Tyr Lys Pro Gln Met Glu Asp
                    165                 170                 175

Gln Lys Tyr Lys Cys Ala Phe Ser Arg Thr Pro Phe Leu Pro Ala Asp
            180                 185                 190

Glu Thr Phe Trp Lys His Phe Leu Thr Leu Lys Met Asn Ile Ser Val
            195                 200                 205

Leu Val Leu Pro Leu Phe Ile Phe Thr Phe Leu Tyr Val Gln Met Arg
            210                 215                 220

Lys Thr Leu Arg Phe Arg Glu Gln Arg Tyr Ser Leu Phe Lys Leu Val
225                 230                 235                 240

Phe Ala Ile Met Val Val Phe Leu Leu Met Trp Ala Pro Tyr Asn Ile
                    245                 250                 255

Ala Phe Phe Leu Ser Thr Phe Lys Glu His Phe Ser Leu Ser Asp Cys
            260                 265                 270

Lys Ser Ser Tyr Asn Leu Asp Lys Ser Val His Ile Thr Lys Leu Ile
            275                 280                 285

Ala Thr Thr His Cys Cys Ile Asn Pro Leu Leu Tyr Ala Phe Leu Asp
            290                 295                 300

Gly Thr Phe Ser Lys Tyr Leu Cys Arg Cys Phe His Leu Arg Ser Asn
305                 310                 315                 320

Thr Pro Leu Gln Pro Arg Gly Gln Ser Ala Gln Gly Thr Ser Arg Glu
                    325                 330                 335

Glu Pro Asp His Ser Thr Glu Val
            340
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

CAGGGAATTC TGAAGATGGC CAATTACACG                                  30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

GCATTTGGTG GATATCAGTT TACACTTCGG                                       30

(2) INFORMATION FOR SEQ ID NO:5:

(i) SEQUENCE CHARACTERISTICS:
             (A) LENGTH: 363 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

ATGAAGGTCT CCGTGGCTGC CCTCTCCTGC CTCATGCTTG TTACTGCCCT TGGATCCCAG       60

GCCCGGGTCA CAAAAGATGC AGAGACAGAG TTCATGATGT CAAAGCTTCC ATTGGAAAAT      120

CCAGTACTTC TGGACAGATT CCATGCTACT AGTGCTGACT GCTGCATCTC CTACACCCCA      180

CGAAGCATCC CGTGTTCACT CCTGGAGAGT TACTTTGAAA CGAACAGCGA GTGCTCCAAG      240

CCGGGTGTCA TCTTCCTCAC CAAGAAGGGG CGACGTTTCT GTGCCAACCC CAGTGATAAG      300

CAAGTTCAGG TTTGCATGAG AATGCTGAAG CTGGACACAC GGATCAAGAC CAGGAAGAAT      360

TGA                                                                   363

(2) INFORMATION FOR SEQ ID NO:6:

(i) SEQUENCE CHARACTERISTICS:
             (A) LENGTH: 120 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:6:

Met Lys Val Ser Val Ala Ala Leu Ser Cys Leu Met Leu Val Thr Ala
  1               5                  10                  15

Leu Gly Ser Gln Ala Arg Val Thr Lys Asp Ala Glu Thr Glu Phe Met
                 20                  25                  30

Met Ser Lys Leu Pro Leu Glu Asn Pro Val Leu Leu Asp Arg Phe His
             35                  40                  45

Ala Thr Ser Ala Asp Cys Cys Ile Ser Tyr Thr Pro Arg Ser Ile Pro
         50                  55                  60

-continued

```
Cys Ser Leu Leu Glu Ser Tyr Phe Glu Thr Asn Ser Glu Cys Ser Lys
 65              70                  75                  80

Pro Gly Val Ile Phe Leu Thr Lys Lys Gly Arg Arg Phe Cys Ala Asn
                 85                  90                  95

Pro Ser Asp Lys Gln Val Gln Val Cys Met Arg Met Leu Lys Leu Asp
            100                 105                 110

Thr Arg Ile Lys Thr Arg Lys Asn
            115             120
```

NUCLEIC ACIDS ENCODING THE G-PROTEIN COUPLED RECEPTOR HNFDS78

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human G-protein coupled receptor, hereinafter referred to as "G-Protein Coupled Receptor HNFDS78".

BACKGROUND OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human 7-transmembrane receptors (G-protein coupled receptors). The invention also relates to inhibiting the action of such polypeptides.

It is well established that many medically significant biological processes are mediated by proteins participating in signal transduction pathways that involve G-proteins and/or second messengers, e.g., cAMP (Lefkowitz, *Nature*, 351:353–354 (1991)). Herein these proteins are referred to as proteins participating in pathways with G-proteins or PPG proteins. Some examples of these proteins include the GPC receptors, such as those for adrenergic agents and dopamine (Kobilka, et al., *PNAS*, 84:46–50 (1987); Kobilka, et al., *Science*, 238:650–656 (1987); Bunzow, et al., *Nature*, 336:783–787 (1988)), G-proteins themselves, effector proteins, e.g., phospholipase C, adenyl cyclase, and phosphodiesterase, and actuator proteins, e.g., protein kinase A and protein kinase C (Simon, et al., *Science*, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include calcitonin, adrenergic, endothelin, cAMP, adenosine, muscarinic, acetylcholine, serotonin, histamine, thrombin, kinin, follicle stimulating hormone, opsins, endothelial differentiation gene-1 receptor, rhodopsins, odorant, cytomegalovirus receptors, etc.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise a hydrophilic socket formed by several G-protein coupled receptors transmembrane domains, which socket is surrounded by hydrophobic residues of the G-protein coupled receptors. The hydrophilic side of each G-protein coupled receptor transmembrane helix is postulated to face inward and form the polar ligand binding site. TM3 has been implicated in several G-protein coupled receptors as having a ligand binding site, such as including the TM3 aspartate residue. Additionally, TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., *Endoc. Rev.*, 10:317–331 (1989)). Different G-protein α-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

Clearly, there is a need for factors that are receptors for chemokines and their roles in dysfunction and disease. There is a need, therefore, for identification and characterization of such factors that are chemokine receptors, and which can play a role in preventing, ameliorating or correcting dysfunctions or diseases.

The polypeptides of the present invention have conserved 7 transmembrane domain residues, and have amino acid sequence homology to known chemokine receptors, such as, for example, CC CKR1 (Ben-Baruch, et al., *J. Biol. Chem.* 270:22123 1995), CC CKR3 (Combadiere, C., *P.M.J. Biol. Chem.* 270:16491 (1995)), CC CKR4 (Power, et al., *J. Biol. Chem.* 270:19495 (1995)) and CC CKR5 (Deng, et al., *Nature* 381:20 (1996); Dragic, et al., *Nature* 381:20 (1996)).

SUMMARY OF THE INVENTION

Toward these ends, and others, it is an object of the present invention to provide polypeptides, inter alia, that have been identified as novel G-Protein Coupled Receptor HNFDS78 by homology between the amino acid sequence set out in FIG. 1 and known amino acid sequences of other proteins, such as, for example, CC CKR1, CC CKR3, CC CKR4 and CC CKR5.

It is a further object of the invention, moreover, to provide polynucleotides that encode G-Protein Coupled Receptor HNFDS78, particularly polynucleotides that encode the polypeptide herein designated G-Protein Coupled Receptor HNFDS78.

In a particularly preferred embodiment of this aspect of the invention, the polynucleotide comprises the region encoding human G-Protein Coupled Receptor HNFDS78 in the sequence set out in FIG. 1.

In accordance with this aspect of the present invention there is provided an isolated nucleic acid molecule encoding a mature polypeptide expressed by the human cDNA contained in ATCC Deposit No. 98099.

In accordance with this aspect of the invention there are provided isolated nucleic acid molecules encoding human G-Protein Coupled Receptor HNFDS78, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of human G-Protein Coupled Receptor HNFDS78.

It also is an object of the invention to provide G-Protein Coupled Receptor HNFDS78 polypeptides, particularly human G-Protein Coupled Receptor HNFDS78 polypeptides, that may be employed for therapeutic purposes, for example, to treat atherosclerosis, inflammatory conditions, and infections, such as bacterial, fungal, protozoan and particularly viral infections, such as, for example, AIDS.

In accordance with this aspect of the invention there are provided novel polypeptides of human origin referred to herein as G-Protein Coupled Receptor HNFDS78 as well as biologically, diagnostically or therapeutically useful fragments, variants and derivatives thereof, variants and derivatives of the fragments, and analogs of the foregoing.

Among the particularly preferred embodiments of this aspect of the invention are variants of human G-Protein Coupled Receptor HNFDS78 encoded by naturally occurring alleles of the human G-Protein Coupled Receptor HNFDS78 gene.

In accordance with another aspect of the present invention there are provided methods of screening for compounds which bind to and activate or inhibit activation of the receptor polypeptides of the present invention and for receptor ligands, such as for example, Chemokine β-8.

It is another object of the invention to provide a process for producing the aforementioned polypeptides, polypeptide fragments, variants and derivatives, fragments of the variants and derivatives, and analogs of the foregoing. In a preferred embodiment of this aspect of the invention there are provided methods for producing the aforementioned G-Protein Coupled Receptor HNFDS78 polypeptides comprising culturing host cells having expressibly incorporated therein an exogenously-derived human G-Protein Coupled Receptor HNFDS78-encoding polynucleotide under conditions for expression of human G-Protein Coupled Receptor HNFDS78 in the host and then recovering the expressed polypeptide.

In accordance with another object the invention there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing G-Protein Coupled Receptor HNFDS78 expression in cells by determining G-Protein Coupled Receptor HNFDS78 polypeptides or G-Protein Coupled Receptor HNFDS78-encoding mRNA; to treat atherosclerosis, stroke, restinosis, inflammatory conditions, and infections, such as bacterial, fungal, protozoan, and particularly viral infections, such as AIDS, in vitro, ex vivo or in vivo by exposing cells to G-Protein Coupled Receptor HNFDS78 polypeptides or polynucleotides as disclosed herein; assaying genetic variation and aberrations, such as defects, in G-Protein Coupled Receptor HNFDS78 genes; and administering a G-Protein Coupled Receptor HNFDS78 polypeptide or polynucleotide to an organism to augment G-Protein Coupled Receptor HNFDS78 function or remediate G-Protein Coupled Receptor HNFDS78 dysfunction.

In accordance with still another embodiment of the present invention there is provided a process of using such activating compounds to stimulate the receptor polypeptide of the present invention for the treatment of conditions related to the under-expression of the G-Protein Coupled Receptor HNFDS78.

In accordance with another aspect of the present invention there is provided a process of using such inhibiting compounds for treating conditions associated with over-expression of the G-Protein Coupled Receptor HNFDS78.

In accordance with yet another aspect of the present invention there is provided non-naturally occurring synthetic, isolated and/or recombinant G-Protein Coupled Receptor HNFDS78 polypeptides which are fragments, consensus fragments and/or sequences having conservative amino acid substitutions, of at least one transmembrane domain of the G-Protein Coupled Receptor HNFDS78 of the present invention, such that the receptor may bind G-Protein Coupled Receptor HNFDS78 ligands, such as for example, Chemokine β-8, or which may also modulate, quantitatively or qualitatively, G-Protein Coupled Receptor HNFDS78 ligand binding, such as binding of, for example, Chemokine β-8.

In accordance with still another aspect of the present invention there are provided synthetic or recombinant G-Protein Coupled Receptor HNFDS78 polypeptides, conservative substitution and derivatives thereof, antibodies, anti-idiotype antibodies, compositions and methods that can be useful as potential modulators of G-Protein Coupled Receptor HNFDS78 function, by binding to ligands, such as binding of, for example, Chemokine β-8, or modulating ligand binding, due to their expected biological properties, which may be used in diagnostic, therapeutic and/or research applications.

It is still another object of the present invention to provide synthetic, isolated or recombinant polypeptides which are designed to inhibit or mimic various G-Protein Coupled Receptor HNFDS78 or fragments thereof, as receptor types and subtypes.

In accordance with certain preferred embodiments of this and other aspects of the invention there are provided probes that hybridize to human G-Protein Coupled Receptor HNFDS78 sequences.

In certain additional preferred embodiments of this aspect of the invention there are provided antibodies against G-Protein Coupled Receptor HNFDS78 polypeptides. In certain particularly preferred embodiments in this regard, the antibodies are highly selective for human G-Protein Coupled Receptor HNFDS78.

In accordance with another aspect of the present invention, there are provided G-Protein Coupled Receptor HNFDS78 agonists. Among preferred agonists are molecules that mimic G-Protein Coupled Receptor HNFDS78, that bind to G-Protein Coupled Receptor HNFDS78-binding molecules or receptor molecules, and that elicit or augment G-Protein Coupled Receptor HNFDS78-induced responses. Also among preferred agonists are molecules that interact with G-Protein Coupled Receptor HNFDS78 or G-Protein Coupled Receptor HNFDS78 polypeptides, or with other modulators of G-Protein Coupled Receptor HNFDS78 activities, and thereby potentiate or augment an effect of G-Protein Coupled Receptor HNFDS78 or more than one effect of G-Protein Coupled Receptor HNFDS78.

In accordance with yet another aspect of the present invention, there are provided G-Protein Coupled Receptor HNFDS78 antagonists. Among preferred antagonists are those which mimic G-Protein Coupled Receptor HNFDS78 so as to bind to G-Protein Coupled Receptor HNFDS78 receptor or binding molecules but not elicit a G-Protein Coupled Receptor HNFDS78-induced response or more than one G-Protein Coupled Receptor HNFDS78-induced response. Also among preferred antagonists are molecules that bind to or interact with G-Protein Coupled Receptor HNFDS78 so as to inhibit an effect of G-Protein Coupled Receptor HNFDS78 or more than one effect of G-Protein Coupled Receptor HNFDS78 or which prevent expression of G-Protein Coupled Receptor HNFDS78.

In a further aspect of the invention there are provided compositions comprising a G-Protein Coupled Receptor HNFDS78 polynucleotide or a G-Protein Coupled Receptor HNFDS78 polypeptide for administration to cells in vitro, to cells ex vivo and to cells in vivo, or to a multicellular organism. In certain particularly preferred embodiments of this aspect of the invention, the compositions comprise a G-Protein Coupled Receptor HNFDS78 polynucleotide for expression of a G-Protein Coupled Receptor HNFDS78 polypeptide in a host organism for treatment of disease. Particularly preferred in this regard is expression in a human patient for treatment of a dysfunction associated with aberrant endogenous activity of G-Protein Coupled Receptor HNFDS78.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIGS. 1A–B shows the nucleotide (SEQ ID NO:1) and deduced amino acid sequence (SEQ ID NO:2) of human G-Protein Coupled Receptor HNFDS78.

FIGS. 2A–B shows the polynucleotide (SEQ ID NO:5) and deduced amino acid (SEQ ID NO:6) sequence of human chemokine β-8.

GLOSSARY

The following illustrative explanations are provided to facilitate understanding of certain terms used frequently herein, particularly in the examples. The explanations are provided as a convenience and are not limitative of the invention.

DIGESTION of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 μg of plasmid or DNA fragment is digested with about 2 units of enzyme in about 20 μl of reaction buffer. For the purpose of isolating DNA fragments for plasmid construction, typically 5 to 50 μg of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

GENETIC ELEMENT generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

ISOLATED means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989) and Maniatis et al., pg. 146, as cited below.

OLIGONUCLEOTIDE(S) refers to relatively short polynucleotides. Often the term refers to single-stranded deoxyribonucleotides, but it can refer as well to single-or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

PLASMIDS generally are designated herein by a lower case p preceded and/or followed by capital letters and/or numbers, in accordance with standard naming conventions that are familiar to those of skill in the art.

Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single-and double-stranded regions, single- and double-stranded RNA, and RNA that is mixture of single- and double-stranded regions, hybrid molecules comprising DNA and RNA that may be In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., Analysis for protein modifications and nonprotein cofactors, Meth. Enzymol. 182:626–646 (1990) and Rattan et al., Protein Synthesis: Posttranslational Modifications and Aging, Ann. N.Y. Acad. Sci. 663:48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a leukaryotic cell. Insect cell often carry out the same post-translational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

RECEPTOR MOLECULE, as used herein, refers to molecules of the present invention, including but not limited to G-Protein Coupled Receptor HNFDS78 polyptides, as well as molecules which bind or interact specifically with G-Protein Coupled Receptor HNFDS78 polypeptides of the present invention, including not only classic receptors, which are preferred, but also other molecules that specifically bind to or interact with polypeptides of the invention (which also may be referred to as "binding molecules" and "interaction molecules," respectively and as "G-Protein Coupled Receptor HNFDS78 binding molecules" and "G-Protein Coupled Receptor HNFDS78 interaction molecules." Binding between polypeptides of the invention and such molecules, including receptor or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention.

Receptors also may be non-naturally occurring, such as antibodies and antibody-derived reagents that bind specifically to polypeptides of the invention.

DESCRIPTION OF THE INVENTION

The present invention relates to novel G-Protein Coupled Receptor HNFDS78 polypeptides and polynucleotides, among other things, as described in greater detail below. In particular, the invention relates to polypeptides and polynucleotides of a novel human G-Protein Coupled Receptor HNFDS78, which is related by amino acid sequence homology to CC CKR1, CC CKR3, CC CKR4 and CC CKR5 polypeptides. The invention relates especially to G-Protein Coupled Receptor HNFDS78 having the nucleotide and amino acid sequences set out in FIG. 1, and to the G-Protein Coupled Receptor HNFDS78 nucleotide and amino acid sequences of the human cDNA in ATCC Deposit No. 98099, which is herein referred to as "the deposited clone" or as the "cDNA of the deposited clone." It will be appreciated that the nucleotide and amino acid sequences set out in FIG. 1 were obtained by sequencing the cDNA of the deposited clone. Hence, the sequence of the deposited clone is controlling as to any discrepancies between the two and any reference to the sequences of FIG. 1 include reference to the sequence of the human cDNA of the deposited clone.

Polynucleotides

In accordance with one aspect of the present invention, there are provided isolated polynucleotides which encode the G-Protein Coupled Receptor HNFDS78 polypeptide having the deduced amino acid sequence of FIG. 1.

Using the information provided herein, such as the polynucleotide sequence set out in FIG. 1, a polynucleotide of the present invention encoding human G-Protein Coupled Receptor HNFDS78 polypeptide may be obtained using standard cloning and screening procedures, such as those for cloning cDNAs using mRNA from cells from microvascular endothelial tissue as starting material. Illustrative of the invention, the microvascular endothelial tissue as starting material. Illustrative of the invention, the polynucleotide set out in FIG. 1 was discovered in a cDNA library derived from cells of human microvascular endothelial tissue.

Human G-Protein Coupled Receptor HNFDS78 of the invention is structurally related to other proteins of the chemokine receptor family, as shown by the results of sequencing the cDNA encoding human G-Protein Coupled Receptor HNFDS78 in the deposited clone. The cDNA sequence thus obtained is set out in FIG. 1. It contains an open reading frame encoding a protein of about 344 amino acid residues with a deduced molecular weight of about 3800 kDa. Approximately the first 20 amino acids represent a putative leader sequence. The protein exhibits greatest homology to CC CKR3 protein among known proteins. G-Protein Coupled Receptor HNFDS78 of FIG. 1 has about 57.5% identity and about 57.5% similarity with the amino acid sequence of CC CKR3.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIG. 1. It also may be a polynucleotide with a different sequence, which, as a result of the redundancy (degeneracy) of the genetic code, encodes the polypeptide of the DNA of FIG. 1.

Polynucleotides of the present invention which encode the polypeptide of FIG. 1 may include, but are not limited to the coding sequence for the mature polypeptide, by itself; the coding sequence for the mature polypeptide and additional coding sequences, such as those encoding a leader or secretory sequence, such as a pre- or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the pQE vector (Qiagen, Inc.), among others, many of which are commercially available. As described in Gentz et al., *Proc. Natl. Acad. Sci., USA* 86: 821–824 (1989), for instance, hexa-histidine provides for convenient purification of the fusion protein. The HA tag corresponds to an epitope derived of influenza hemagglutinin protein, which has been described by Wilson et al., *Cell* 37:767 (1984), for instance.

In accordance with the foregoing, the term "polynucleotide encoding a polypeptide" as used herein encompasses polynucleotides which include a sequence encoding a polypeptide of the present invention, particularly the human G-Protein Coupled Receptor HNFDS78 having the amino acid sequence set out in FIG. 1. The term also encompasses polynucleotides that include a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the polypeptide having the deduced amino acid sequence of FIG. 1. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of G-Protein Coupled Receptor HNFDS78 set out in FIG. 1; variants, analogs, derivatives and fragments thereof, and fragments of the variants, analogs and derivatives.

Further particularly preferred in this regard are polynucleotides encoding G-Protein Coupled Receptor HNFDS78 variants, analogs, derivatives and fragments, and variants, analogs and derivatives of the fragments, which have the amino acid sequence of the G-Protein Coupled Receptor HNFDS78 polypeptide of FIG. 1 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the G-Protein Coupled Receptor HNFDS78. Also especially preferred in this regard are conservative substitutions. Most highly preferred are polynucleotides encoding polypeptides having the amino acid sequence of FIG. 1, without substitutions.

Further preferred embodiments of the invention are polynucleotides that are at least 70% identical to a polynucleotide encoding the G-Protein Coupled Receptor HNFDS78 polypeptide having the amino acid sequence set out in FIG. 1, and polynucleotides which are complementary to such polynucleotides. Alternatively, most highly preferred are polynucleotides that comprise a region that is at least 80% identical to a polynucleotide encoding the G-Protein Coupled Receptor HNFDS78 polypeptide of the human cDNA of the deposited clone and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiments in this respect, moreover, are polynucleotides which encode polypeptides which retain substantially the same biological function or activity as the mature polypeptide encoded by the cDNA of FIG. 1.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for cDNA and genomic DNA to isolate full-length cDNAs and genomic clones encoding G-Protein Coupled Receptor HNFDS78 and to isolate cDNA and genomic clones of other genes that have a high sequence similarity to the human G-Protein Coupled Receptor HNFDS78 gene. Such probes generally will comprise at least 15 bases. Preferably, such probes will have at least 30 bases and may have at least 50 bases. Particularly preferred probes will have at least 30 bases and will have 50 bases or less.

For example, the coding region of the G-Protein Coupled Receptor HNFDS78 gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease, as further discussed herein relating to polynucleotide assays, inter alia.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited Materials

A deposit containing a human G-Protein Coupled Receptor HNFDS78 cDNA has been deposited with the American Type Culture Collection, as noted above. Also as noted above, the human cDNA deposit is referred to herein as "the deposited clone" or as "the cDNA of the deposited clone."

The deposited clone was deposited with the American Type Culture Collection, 12301 Park Lawn Drive, Rockville, Md. 20852, USA, on Jul. 3, 1996, and assigned ATCC Deposit No. 98099.

The deposited material is a recombinant *Escherichia coli* that contains the full length G-Protein Coupled Receptor HNFDS78 cDNA, referred to as "*Escherichia coli* HGS HNFDS78 (ATG 798)" upon deposit.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a human G-Protein Coupled Receptor HNFDS78 polypeptide which has the deduced amino acid sequence of FIG. 1.

The invention also relates to fragments, analogs and derivatives of these polypeptides. The terms "fragment," "derivative" and "analog" when referring to the polypeptide of FIG. 1, means a polypeptide which retains essentially the same biological function or activity as such polypeptide, i.e. functions as a G-Protein Coupled Receptor HNFDS78, or retains the ability to bind ligand or the receptor even though the polypeptide does not function as a G-Protein Coupled Receptor HNFDS78, for example, a soluble form of the receptor. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIG. 1 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of G-Protein Coupled Receptor HNFDS78 set out in FIG. 1, variants, analogs, derivatives and fragments thereof, and variants, analogs and derivatives of the fragments. Alternatively, particularly preferred embodiments of the invention in this regard are polypeptides having the amino acid sequence of the G-Protein Coupled Receptor HNFDS78, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the G-Protein Coupled Receptor HNFDS78 polypeptide of FIG. 1, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the G-Protein Coupled Receptor HNFDS78. Also especially preferred in this regard are conservative substitutions. Most highly preferred are polypeptides having the amino acid sequence of FIG. 1 without substitutions.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 80% identity to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide. Moreover, also known in the art is "identity" which means the degree of sequence relatedness between two polypeptide or two polynucleotides sequences as determined by the identity of the match between two strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity and similarity between two polynucleotide or polypeptide sequences, the terms "identity" and "similarity" are well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., SIAM J. Applied Math., 48: 1073 (1988). Methods commonly employed to determine identity or similarity between two sequences include, but are not limited to disclosed in Guide to Huge Computers, Martin J. Bishop, ed., Academic Press, San Diego, 1994, and Carillo, H., and Lipman, D., SIAM J. Applied Math. 48:1073 (1988). Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, et al., *Nucleic Acids Research* 12(1):387 (1984)), BLASTP, BLASTN, FASTA (Atschul, et al., *J. Molec. Biol.* 215:403 (1990)).

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of G-Protein Coupled Receptor HNFDS78, most particularly fragments of the G-Protein Coupled Receptor HNFDS78 having the amino acid set out in FIG. 1, and fragments of variants and derivatives of the G-Protein Coupled Receptor HNFDS78 of FIG. 1.

In this regard a fragment is a polypeptide having an amino acid sequence that entirely is the same as part but not all of the amino acid sequence of the aforementioned G-Protein Coupled Receptor HNFDS78 polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a G-Protein Coupled Receptor HNFDS78 polypeptide of the present comprised within a precursor polypeptide designed for expression in a host and having heterologous pre and pro-polypeptide regions fused to the amino terminus of the G-Protein Coupled Receptor HNFDS78 fragment and an additional region fused to the carboxyl terminus of the fragment. Therefore, fragments in one aspect of the meaning intended herein, refers to the portion or portions of a fusion polypeptide or fusion protein derived from G-Protein Coupled Receptor HNFDS78.

As representative examples of polypeptide fragments of the invention, there may be mentioned those which have from about 5–15, 10–20, 15–40, 30–55, 41–75, 41–80, 41–90, 50–100, 75–100, 90–115, 100–125, and 110–113 amino acids long.

In this context about includes the particularly recited range and ranges larger or smaller by several, a few, 5, 4, 3, 2 or 1 amino acid at either extreme or at both extremes. For instance, about 40–90 amino acids in this context means a polypeptide fragment of 40 plus or minus several, a few, 5, 4, 3, 2 or 1 amino acids to 90 plus or minus several a few, 5, 4, 3, 2 or 1 amino acid residues, i.e., ranges as broad as 40 minus several amino acids to 90 plus several amino acids to as narrow as 40 plus several amino acids to 90 minus several amino acids.

Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 5–15, 10–20, 15–40, 30–55, 41–75, 41–80, 41–90, 50–100, 75–100, 90–115, 100–125, and 110–113 acids long.

Among especially preferred fragments of the invention are truncation mutants of G-Protein Coupled Receptor HNFDS78. Truncation mutants include G-Protein Coupled Receptor HNFDS78 polypeptides having the amino acid sequence of FIG. 1, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally.

Also preferred in this aspect of the invention are fragments characterized by structural or functional attributes of G-Protein Coupled Receptor HNFDS78. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of G-Protein Coupled Receptor HNFDS78.

Among highly preferred fragments in this regard are those that comprise regions of G-Protein Coupled Receptor HNFDS78 that combine several structural features, such as several of the features set out above. In this regard, the regions defined by the residues about 10 to about 20, about 40 to about 50, about 70 to about 90 and about 100 to about 113 of FIG. 1, which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of G-Protein Coupled Receptor HNFDS78. Most highly preferred in this regard are fragments that have a chemical, biological or other activity of G-Protein Coupled Receptor HNFDS78, including those with a similar activity or an improved activity, or with a decreased undesirable activity. Highly preferred in this regard are fragments that contain regions that are homologs in sequence, or in position, or in both sequence and to active regions of related polypeptides, such as the related polypeptides which include chemokine receptors CC CKR1, CC CKR3, CC CKR4, and CC CKR5. Among particularly preferred fragments in these regards are truncation mutants, as discussed above.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above.

Vectors, Host cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques. In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skilled in the art, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Hosts for of a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the E. coli lacI and lacZ promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. *BASIC METHODS IN MOLECULAR BIOLOGY*, (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in manmmalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *MOLECULAR CLONING: A LABORATORY MANUAL*, 2nd Ed., Cold Spring Harbor Laboratory Press, Cold Spring Harbor, N.Y. (1989).

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of *E. coli* and the trp 1 gene of *S. cerevisiae*.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunolglobulin that is useful to solubilize receptors. For example, EP-A-O 464 533 (Canadian counterpart 2045869) discloses fusion proteins comprising various portions of constant region of immunoglobin molecules together with another human protein or part thereof. In many cases, the Fc part in fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, shIL5- has been fused with Fc portions for the purpose of high-throughput screening assays to identify antagonists of hIL-5. See, D. Bennett et al., *Journal of Molecular Recognition* 8:8 52–58 (1995) and K. Johanson et al., *The Journal of Biological Chemistry* 270:16, pp 9459–9471 (1995).

Suitable prokaryotic hosts for propagation, maintenance or expression of polynucleotides and polypeptides in accordance with the invention include *Escherichia coli, Bacillus subtilis* and *Salmonella typhimurium*. Various species of Pseudomonas, Streptomyces, and Staphylococcus are suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. Examples of mammalian expression systems include the COS-7 lines of monkey kidney fibroblast, described in Gluzman et al., *Cell* 23:175 (1981). Other cell lines capable of expressing a compatible vector include for example, the C127, 3T3, CHO, HeLa, human kidney 293 and BHK cell lines.

Mammalian expression vectors will comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

The G-Protein Coupled Receptor HNFDS78 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and marnmalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

G-Protein Coupled Receptor HNFDS78 polynucleotides and polypeptides may be used in accordance with the present invention for a variety of applications, particularly those that make use of the chemical and biological properties of G-Protein Coupled Receptor HNFDS78. Additional applications relate to diagnosis and to treatment of disorders of cells, tissues and organisms. These aspects of the invention are illustrated further by the following discussion.

Polynucleotide Assays

This invention is also related to the use of the G-Protein Coupled Receptor HNFDS78 polynucleotides to detect complementary polynucleotides such as, for example, as a diagnostic reagent. Detection of a mutated form of G-Protein Coupled Receptor HNFDS78 associated with a dysfunction will provide a diagnostic tool that can add or define a diagnosis of a disease or susceptibility to a disease which results from under-expression over-expression or altered expression of G-Protein Coupled Receptor HNFDS78. Individuals carrying mutations in the human G-Protein Coupled Receptor HNFDS78 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. PCR (Saiki et al., *Nature*, 324: 163–166 (1986)). RNA or cDNA may also be used in the same ways. As an example, PCR primers complementary to the nucleic acid encoding G-Protein Coupled Receptor HNFDS78 can be used to identify and analyze G-Protein Coupled Receptor HNFDS78 expression and mutations. For example, deletions and insertions can be detected by a change in size of the amplified product in comparison to the normal genotype. Point mutations can be identified by hybridizing amplified DNA to radiolabeled G-Protein Coupled Receptor HNFDS78 RNA or alternatively, radiolabeled G-Protein Coupled Receptor HNFDS78 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230: 1242 (1985)).

Sequence changes at specific locations also may be revealed by nuclease protection assays, such as RNase and S1 protection or the chemical cleavage method (e.g., Cotton et al., *Proc. Natl. Acad. Sci., USA*, 85:4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

In accordance with a further aspect of the invention, there is provided a process for detecting or determining atherosclerosis, restinosis, stroke, inflammatory disease, and infections, such as bacterial, fungal, protozoan, and particularly viral infections, such as, those caused by, for example, HIV-1 or HIV-2, or a susceptibility to any of these diseases. Thus, a mutation in G-Protein Coupled Receptor HNFDS78 indicates a susceptibility to atherosclerosis, restinosis, stroke, inflammatory disease, and infections, such as viral infections, particularly those caused by HIV-1 or HIV-2, and the nucleic acid sequences described above may be employed in an assay for ascertaining such susceptibility. Thus, for example, the assay may be employed to determine a mutation in a human G-Protein Coupled Receptor HNFDS78 protein as herein described, such as a deletion, truncation, insertion, frame shift, etc., with such mutation being indicative of a susceptibility to atherosclerosis, restinosis, stroke, inflammatory disease, and infections, such as bacterial, fungal, protozoan, and particularly viral infections, such as those caused by, for example, HIV-1 or HIV-2.

A mutation may be ascertained for example, by a DNA sequencing assay. Tissue samples, including but not limited to blood samples are obtained from a human patient. The samples are processed by methods known in the art to capture the RNA. First strand cDNA is synthesized from the RNA samples by adding an oligonucleotide primer consisting of polythymidine residues which hybridize to the polyadenosine stretch present on the mRNA's. Reverse transcriptase and deoxynucleotides are added to allow synthesis of the first strand cDNA. Primer sequences are synthesized based on the DNA sequence of the DNA repair protein of the invention. The primer sequence is generally comprised of at least 15 consecutive bases, and may contain at least 30 or even 50 consecutive bases.

RT-PCR can also be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding G-Protein Coupled Receptor HNFDS78 can be used to identify and analyze mutations. Examples of representative primers are shown below in Table 1. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

TABLE 1

Primers Used for Detection of Mutations in G-Protein Coupled Receptor HNFDS78 Gene

5'-CAGGGAATTCTGAAGATGGCCAATTACACG-3' [SEQ ID NO:3]

5'-GCATTTGGTGGATATCAGTTTACACTTCGG-3' [SEQ ID NO:4]

The above primers may be used for amplifying G-Protein Coupled Receptor HNFDS78 cDNA isolated from a sample derived from a patient. The invention also provides the primers of Table 1 with 1, 2, 3 or 4 nucleotides removed from the 5' and/or the 3' end. The primers may be used to amplify the gene isolated from the patient such that the gene may then be subject to various techniques for elucidation of the DNA sequence. In this way, mutations in the DNA sequence may be diagnosed.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230:1242 (1985)).

Sequence changes at specific locations may also be revealed by nuclease protection assays, such as RNase and S1 protection or the chemical cleavage method (e.g., Cotton et al., *PNAS, USA*, 85:4397–4401 (1985)).

Thus, the detection of a specific DNA sequence and/or quantitation of the level of the sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA. The invention provides a process for diagnosing, disease, particularly atherosclerosis, restinosis, stroke, inflammatory disease, and infections, such as bacterial, fungal, protozoan infections, and particularly viral infections, such as those caused by, for example HIV-1 or HIV-2, and most particularly cardiovascular disease and infectious disease, comprising determining from a sample derived from a patient a decreased level of expression of polynucleotide having the sequence of FIG. 1 (SEQ ID NO: 1). Decreased expression of polynucleotide can be measured using any on of the methods well known in the art for the quantitation of polynucleotides, such as, for example, PCR, RT-PCR, RNase protection, Northern blotting and other hybridization methods.

In addition to more conventional gel-electrophoresis and DNA sequencing, mutations can also be detected by in situ analysis.

Fluorescence in situ hybridization (FISH) of a cDNA clone to a metaphase chromosomal spread can be used to provide a precise chromosomal location.

As an example of how this was performed, G-Protein Coupled Receptor HNFDS78 DNA was digested and purified with QIAEX II DNA purification kit (QIAGEN, Inc., Chatsworth, Calif.) and ligated to Super Cos1 cosmid vector (STRATAGENE, La Jolla, Calif.). DNA was purified using Qiagen Plasmid Purification Kit (QIAGEN Inc., Chatsworth, Calif.) and 1 mg was labeled by nick translation in the presence of Biotin-dATP using BioNick Labeling Kit (GibcoBRL, Life Technologies Inc., Gaithersburg, Md.). Biotinilation was detected with GENE-TECT Detection System (CLONTECH Laboratories, Inc. Palo Alto, Calif.). In situ Hybridization was performed on slides using ONCOR Light Hybridization Kit (ONCOR, Gaithersberg, Md.) to detect single copy sequences on metaphase chromosomes. Peripheral blood of normal donors was cultured for three days in RPMI 1640 supplemented with 20% FCS, 3% PHA and penicillin/streptomycin, synchronized with $10^{-7}$ M methotrexate for 17 hours and washed twice with unsupplemented RPMI. Cells were incubated with $10^{-3}$ M thymidine for 7 hours. The cells were arrested in metaphase after 20 minutes incubation with colcemid (0.5 $\mu$g/ml) followed by hypotonic lysis in 75 mM KCl for 15 minutes at 37° C. Cell pellets were then spun out and fixed in Carnoy's fixative (3:1 methanol/acetic acid).

Metaphase spreads were prepared by adding a drop of the suspension onto slides and aid dried. Hybridization was performed by adding 100 ng of probe suspended in 10 ml of hybridization mix (50% formamide, 2×SSC, 1% dextran sulfate) with blocking human placental DNA 1 $\mu$g/ml), Probe mixture was denatured for 10 minutes in 70° C. water bath and incubated for 1 hour at 37° C., before placing on a prewarmed (37° C.) slide, which was previously denatured in 70% formamide/2xSSC at 70° C., and dehydrated in ethanol series, chilled to 4° C.

Slides were incubated for 16 hours at 37° C. in a humidified chamber. Slides were washed in 50% formamide/2× SSC for 10 minutes at 41° C. and 2×SSC for 7 minutes at 37° C. Hybridization probe was detected by incubation of the slides with FITC-Avidin (ONCOR, Gaithersberg, Md.), according to the manufacturer protocol. Chromosomes were counterstained with propridium iodine suspended in mounting medium. Slides were visualized using a Leitz ORTHO-PLAN 2-epifluorescence microscope and five computer images were taken using Imagenetics Computer and MacIntosh printer. G-Protein Coupled Receptor HNFDS78 maps to chromosome 3p21.

Once a sequence has been mapped to a precise chromosomal location, the physical position of the sequence on the chromosome can be correlated with genetic map data. Such data are found, for example, in V. McKusick, Mendelian Inheritance in Man, which is publicly available on line via computer. The relationship between genes and diseases that have been mapped to the same chromosomal region are then identified through linkage analysis (Co-Inheritance of Physically Adjacent Genes).

Unless otherwise stated, transformation was performed as described in the method of Graham, F. and Van der Eb, A., *Virology*, 52:456–457 (1973).

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a G-Protein Coupled Receptor HNFDS78 gene. This can be accomplished using a variety of well known techniques and libraries, which generally are available commercially. The genomic DNA the is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with cDNA as short as 50 or 60. For a review of this technique, see Verma et al., HUMAN CHROMOSOMES: A MANUAL OF BASIC TECHNIQUES, Pergamon Press, New York (1988).

Once a sequence has been mapped to a precise chromosomal location, the physical position of the sequence on the chromosome can be correlated with genetic map data. Such data are found, for example, in V. McKusick, MENDELIAN INHERITANCE IN MAN, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Polypeptide Assays

The present invention also relates to a diagnostic assays such as quantitative and diagnostic assays for detecting levels of G-Protein Coupled Receptor HNFDS78 protein in cells and tissues, including determination of normal and abnormal levels. Thus, for instance, a diagnostic assay in accordance with the invention for detecting over-expression of G-Protein Coupled Receptor HNFDS78 protein compared to normal control tissue samples may be used to detect the presence of a tumor, for example. Assay techniques that can be used to determine levels of a protein, such as an G-Protein Coupled Receptor HNFDS78 protein of the present invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to G-Protein Coupled Receptor HNFDS78, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA a sample is removed from a host and incubated on a solid support, e.g., a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any G-Protein Coupled Receptor HNFDS78 proteins attached to the polystyrene dish. Unbound monoclonal antibody is washed out with buffer. The reporter antibody linked to horseradish peroxidase is placed in the dish resulting in binding of the reporter antibody to any monoclonal antibody bound to G-Protein Coupled Receptor HNFDS78. Unattached reporter antibody is then washed out. Reagents for peroxidase activity, including a calorimetric substrate are then added to the dish. Immobilized peroxidase, linked to G-Protein Coupled Receptor HNFDS78 through the primary and secondary antibodies, produces a colored reaction product. The amount of color developed in a given time period indicates the amount of G-Protein Coupled Receptor HNFDS78 protein present in the sample. Quantitative results typically are obtained by reference to a standard curve.

A competition assay may be employed wherein antibodies specific to G-Protein Coupled Receptor HNFDS78 attached to a solid support and labeled G-Protein Coupled Receptor HNFDS78 and a sample derived from the host are passed over the solid support and the amount of label detected attached to the solid support can be correlated to a quantity of G-Protein Coupled Receptor HNFDS78 in the sample.

Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, et al., Nature 256:495–497 (1975), the trioma technique, the human B-cell hybridoma technique (Kozbor, et al., Immunology Today 4:72 (1983) and the EBV-hybridoma technique to produce human monoclonal antibodies (Cole et al., pg. 77–96 in MONOCLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Thus, among others, antibodies against G-Protein Coupled Receptor HNFDS78 may be employed to inhibit hypertension, angina pectoris, myocardial infarction, ulcers, Alzheimer's disease, stroke, inflammation (chronic and acute), CNS inflammation, asthma, allergies, neurodegenerative disease, head injury induced neurodegenerative disease, benign prostatic hypertrophy and psychotic and neurological disorders, including schizophrenia, manic excitement, depression, delirium, dementia or severe mental retardation, dyskinesias, such as Huntington's disease or Gilles dela Tourett's syndrome, bacterial infections, fungal infections, protozoan infections, and viral infections, among others. Antibodies which inhibit G-protein coupled receptors are also been useful in reversing endogenous anorexia and in the control of bulimia. Antibodies which inhibit G-Protein Coupled Receptor HNFDS78 are also useful in inhibiting binding of bacterial cells, fungal cells, protozoan cells, and virus and also in inhibiting bacterial infection, fungal infection, protozoan infection and viral infection, particularly HIV-1 binding and infection or HIV-2 binding and infection.

G-Protein Coupled Receptor HNFDS78 Binding Molecules and Assays

This invention also provides a method for identification of molecules, such as receptor molecules, that bind G-Protein Coupled Receptor HNFDS78. Genes encoding proteins that bind G-Protein Coupled Receptor HNFDS78, such as receptor proteins, can be identified by numerous methods known to those of skill in the art, for example, ligand panning and FACS sorting. Such methods are described in many laboratory manuals such as, for instance, Coligan et al., Current Protocols in Immunology 1(2): Chapter 5 (1991).

For instance, expression cloning may be employed for this purpose. To this end polyadenylated RNA is prepared from a cell responsive to G-Protein Coupled Receptor HNFDS78, a cDNA library is created from this RNA, the library is divided into pools and the pools are transfected individually into cells that are not responsive to G-Protein Coupled Receptor HNFDS78. The transfected cells then are exposed to labeled G-Protein Coupled Receptor HNFDS78. (G-Protein Coupled Receptor HNFDS78 can be labeled by a variety of well-known techniques including standard methods of radio-iodination or inclusion of a recognition site for a site-specific protein kinase.) Following exposure, the cells are fixed and binding of G-Protein Coupled Receptor HNFDS78 is determined. These procedures conveniently are carried out on glass slides.

Pools are identified of cDNA that produced G-Protein Coupled Receptor HNFDS78-binding cells. Sub-pools are prepared from these positives, transfected into host cells and screened as described above. Using an iterative sub-pooling and re-screening process, one or more single clones that encode the putative binding molecule, such as a receptor molecule, can be isolated.

Alternatively a labeled ligand can be photoaffinity linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to assess G-Protein Coupled Receptor HNFDS78 binding capacity of G-Protein Coupled Receptor HNFDS78 binding molecules, such as receptor molecules, in cells or in cell-free preparations.

The G-Protein Coupled Receptor HNFDS78 of the present invention may be employed in a process for screening for compounds which activate (agonists) or inhibit activation (antagonists) of the receptor polypeptide of the present invention.

In general, such screening procedures involve providing appropriate cells which express the receptor polypeptide of the present invention on the surface thereof. Such cells include cells from mammals, yeast, drosophila or *E. Coli*. In particular, a polynucleotide encoding the receptor of the present invention is employed to transfect cells to thereby express the G-Protein Coupled Receptor HNFDS78. The expressed receptor is then contacted with a test compound to observe binding, stimulation or inhibition of a functional response.

One such screening procedure involves the use of melanophores which are transfected to express the G-Protein Coupled Receptor HNFDS78 of the present invention. Such a screening technique is described in PCT WO 92/01810 published Feb. 6, 1992.

Thus, for example, such assay may be employed for screening for a compound which inhibits activation of the receptor polypeptide of the present invention by contacting the melanophore cells which encode the receptor with both the receptor ligand and a compound to be screened. Inhibition of the signal generated by ligand indicates that a compound is a potential antagonist for the receptor, i.e., inhibits activation of the receptor.

The screen may be employed for determining a compound which activates the receptor by contacting such cells with compounds to be screened and determining whether such compound generates a signal, i.e., activates the receptor.

Other screening techniques include the use of cells which express the G-Protein Coupled Receptor HNFDS78 (for example, transfected CHO cells) in a system which measures extracellular pH changes caused by receptor activation, for example, as described in *Science* 246:181–296 (October 1989). For example, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding the G-Protein Coupled Receptor HNFDS78 into Xenopus oocytes to transiently express the receptor. The receptor oocytes may then be contacted with a receptor ligand, such as for example, Chemokine β-8, and a compound to be screened, followed by detection of inhibition or activation of a signal, e.g., proton, and other ion signal, but particularly calcium ion signal, in screening for compounds which are thought to inhibit activation of the receptor.

Another screening technique involves expressing the G-Protein Coupled Receptor HNFDS78 in which the receptor is linked to, e.g., phospholipase C or D or other proteins. As representative examples of such cells, there may be mentioned endothelial cells, smooth muscle cells, embryonic kidney cells, etc. The screening may be accomplished as hereinabove described by detecting activation of the receptor or inhibition of activation of the receptor from a second signal, such as for example, phospholipase or other activated/expressed protein.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the G-Protein Coupled Receptor HNFDS78 such that the cell expresses the receptor on its surface and contacting the cell with a compound in the presence of a labeled form of a known ligand. Ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

G-Protein Coupled Receptor HNFDS78 are ubiquitous in the mammalian host and are responsible for many biological functions, including many pathologies. Accordingly, it is desirous to find compounds and drugs which stimulate the G-Protein Coupled Receptor HNFDS78 on the one hand and which can inhibit the function of a G-Protein Coupled Receptor HNFDS78 on the other hand.

For example, compounds which activate the G-Protein Coupled Receptor HNFDS78 may be employed for therapeutic purposes, such as the treatment of cancer and infectious disease.

In general, compounds which inhibit activation of the G-Protein Coupled Receptor HNFDS78 may be employed for a variety of therapeutic purposes, for example, for the treatment of hypertension, angina pectoris, myocardial infarction, ulcers, Alzheimer's disease, stroke, atherosclerosis, inflammation (chronic and acute), CNS inflammation, asthma, allergies, neurodegenerative disease, head injury induced neurodegenerative disease, benign prostatic hypertrophy and psychotic and neurological disorders, including schizophrenia, manic excitement, depression, delirium, dementia or severe mental retardation, dyskinesias, such as Huntington's disease or Gilles dela Tourett's syndrome, and infections, such as those caused by bacteria, fungi, protozoa and virus, among others. Compounds which inhibit G-protein coupled receptors have also been useful in reversing endogenous anorexia and in the control of bulimia. Compounds which inhibit G-Protein Coupled Receptor HNFDS78 are also been useful in inhibiting the binding of bacteria, fungi, protozoa and virus, and also inhibiting infection caused by bacteria, fungi, protozoa, and virus, and particularly for inhibiting HIV-1 binding and infection or HIV-2 binding and infection.

An antibody may antagonize a G-Protein Coupled Receptor HNFDS78 of the present invention, or in some cases an oligopeptide, which bind to the G-Protein Coupled Receptor HNFDS78 but does not elicit a second messenger response such that the activity of the G-Protein Coupled Receptor HNFDS78 is prevented. Antibodies include anti-idiotypic antibodies which recognize unique determinants generally associated with the antigen-binding site of an antibody. Potential antagonist compounds also include proteins which are closely related to a ligand of the G-Protein Coupled Receptor HNFDS78, i.e. a fragment of a ligand, which have lost biological function and when binding to the G-Protein Coupled Receptor HNFDS78, elicit no response.

An antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al, *Science*, 241:456 (1988); and Dervan et al., *Science*, 251:1360 (1991)), thereby preventing transcription and the production of G-Protein Coupled Receptor HNFDS78. The antisense RNA oligonucleotide hybridizes to the mRNA in vivo and blocks translation of mRNA molecules into G-Protein Coupled Receptor HNFDS78 (antisense—Okano, *J Neurochem.*, 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-Protein Coupled Receptor HNFDS78.

A small molecule which binds to the G-Protein Coupled Receptor HNFDS78, making it inaccessible to ligands such that normal biological activity is prevented, for example small peptides or peptide-like molecules, may also be used to inhibit activation of the receptor polypeptide of the present invention.

A soluble form of the G-Protein Coupled Receptor HNFDS78, e.g. a fragment of the receptors, may be used to inhibit activation of the receptor by binding to a ligand to a polypeptide of the present invention and preventing ligand from interacting with membrane bound G-Protein Coupled Receptor HNFDS78.

This invention additionally provides a method of treating an abnormal condition related to an excess of G-Protein Coupled Receptor HNFDS78 activity which comprises administering to a subject the inhibitor compounds as hereinabove described along with a pharmaceutically acceptable carrier in an amount effective to inhibit activation by blocking binding of ligands to the G-Protein Coupled Receptor HNFDS78, or by inhibiting a second signal, and thereby alleviating the abnormal conditions.

The invention also provides a method of treating abnormal conditions related to an under-expression of G-Protein Coupled Receptor HNFDS78 activity which comprises administering to a subject a therapeutically effective amount of a compound which activates the receptor polypeptide of the present invention as described above in combination with a pharmaceutically acceptable carrier, to thereby alleviate the abnormal conditions.

The soluble form of the G-Protein Coupled Receptor HNFDS78, and compounds which activate or inhibit such receptor, may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

Agonists and Antagonists—Assays and Molecules

The invention also provides a method of screening compounds to identify those which enhance or block the action of G-Protein Coupled Receptor HNFDS78 on cells, such as its interaction with G-Protein Coupled Receptor HNFDS78-binding molecules such as receptor molecules. An agonist is a compound which increases the natural biological functions of G-Protein Coupled Receptor HNFDS78 or which functions in a manner similar to G-Protein Coupled Receptor HNFDS78, while antagonists decrease or eliminate such functions.

For example, a cellular compartment, such as a membrane or a preparation thereof, such as a membrane-preparation, may be prepared from a cell that expresses a molecule that binds G-Protein Coupled Receptor HNFDS78, such as a molecule of a signaling or regulatory pathway modulated by G-Protein Coupled Receptor HNFDS78. The preparation is incubated with labeled G-Protein Coupled Receptor HNFDS78 in the absence or the presence of a candidate molecule which may be a G-Protein Coupled Receptor HNFDS78 agonist or antagonist. The ability of the candidate molecule to bind the binding molecule is reflected in decreased binding of the labeled ligand. Molecules which bind gratuitously, i.e., without inducing the effects of G-Protein Coupled Receptor HNFDS78 on binding the G-Protein Coupled Receptor HNFDS78 binding molecule, are most likely to be good antagonists. Molecules that bind well and elicit effects that are the same as or closely related to G-Protein Coupled Receptor HNFDS78 are agonists.

G-Protein Coupled Receptor HNFDS78-like effects of potential agonists and antagonists may by measured, for instance, by determining activity of a second messenger system following interaction of the candidate molecule with a cell or appropriate cell preparation, and comparing the effect with that of G-Protein Coupled Receptor HNFDS78 or molecules that elicit the same effects as G-Protein Coupled Receptor HNFDS78. Second messenger systems that may be useful in this regard include but are not limited to AMP guanylate cyclase, ion channel or phosphoinositide hydrolysis second messenger systems.

Another example of an assay for G-Protein Coupled Receptor HNFDS78 antagonists is a competitive assay that combines G-Protein Coupled Receptor HNFDS78 and a potential antagonist with membrane-bound G-Protein Coupled Receptor HNFDS78 receptor molecules or recombinant G-Protein Coupled Receptor HNFDS78 receptor molecules under appropriate conditions for a competitive inhibition assay. G-Protein Coupled Receptor HNFDS78 can be labeled, such as by radioactivity, such that the number of G-Protein Coupled Receptor HNFDS78 molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing G-Protein Coupled Receptor HNFDS78-induced activities, thereby preventing the action of G-Protein Coupled Receptor HNFDS78 by excluding G-Protein Coupled Receptor HNFDS78 from binding.

Potential antagonists include a small molecule which binds to and occupies the binding site of the polypeptide thereby preventing binding to cellular binding molecules, such as receptor molecules, such that normal biological activity is prevented. Examples of small molecules include but are not limited to small organic molecules, peptides or peptide-like molecules.

Other potential antagonists include antisense molecules. Antisense technology can be used to control gene expression through antisense DNA or RNA or through triple-helix formation. Antisense techniques are discussed, for example, in—Okano, *J. Neurochem.* 56:560 (1991); OLIGODEOXY-NUCLEOTIDES AS ANTISENSE INHIBITORS OF GENE EXPRESSION, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of G-Protein Coupled Receptor HNFDS78. The antisense RNA oligonucleotide hybridizes to the mRNA in vivo and blocks translation of the mRNA molecule into G-Protein Coupled Receptor HNFDS78 polypeptide. The oligonucleotides described above can also be delivered to cells such that the antisense RNA or DNA may be expressed in vivo to inhibit production of G-Protein Coupled Receptor HNFDS78.

The antagonists may be employed in a composition with a pharmaceutically acceptable carrier, e.g., as hereinafter described.

The antagonists may be employed for instance to inhibit hypertension, angina pectoris, myocardial infarction, ulcers, Alzheimer's disease, stroke, atherosclerosis, inflammation (chronic and acute), CNS inflammation, asthma, allergies, neurodegenerative disease, head injury induced neurodegenerative disease, benign prostatic hypertrophy and psychotic and neurological disorders, including schizophrenia, manic excitement, depression, delirium, dementia or severe mental retardation, dyskinesias, such as Huntington's disease or Gilles dela Tourett's syndrome, and bacterial infections, fungal infections, and viral infections, among others. Antagonists of the invention are also useful in reversing endogenous anorexia and in the control of bulimia and in inhibiting binding of bacteria, fungi, protozoa and virus, and also for inhibiting bacterial infection, fungal infection, protozoan infection and viral infection, particularly for inhibiting HIV-1 binding and infection or HIV-2 binding and infection.

The agonists may be employed in a composition with a pharmaceutically acceptable carrier, e.g., as hereinafter described.

The agonists may be employed for instance to treat autoimmune diseases, infectious diseases and cancer.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 μg/kg body weight. In most cases they will be administered in an amount not in excess of about 8 mg/kg body weight per day. Preferably, in most cases, dose is from about 10 μg/kg to about 1 mg/kg body weight, daily. It will be appreciated that optimum dosage will be determined by standard methods for each treatment modality and indication, taking into account the indication, its severity, route of administration, complicating conditions and the like.

Gene Therapy

The G-Protein Coupled Receptor HNFDS78 polynucleotides, polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirtis (CMV) promoter described in Miller et al., *Biotechniques* 7:980–990 (1989), or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP+E-86, GP+envAm12, and DAN cell lines as described in Miller, A., *Human Gene Therapy* 1:5–14 (1990). The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., *MOLECULAR CLONING: A LABORATORY MANUAL*, 2nd Ed.; Cold Spring Harbor Laboratory Press, Cold Spring Harbor, N.Y. (1989), herein referred to as "Sambrook."

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook and numerous other references such as, for instance, by Goeddel et al., *Nucleic Acids Res.* 8:4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 $\mu$g of DNA.

Example 1

Expression and purification of human G-Protein Coupled Receptor HNFDS78 using bacteria The DNA sequence encoding human G-Protein Coupled Receptor HNFDS78 in the deposited polynucleotide was amplified using PCR oligonucleotide primers specific to the amino acid carboxyl terminal sequence of the human G-Protein Coupled Receptor HNFDS78 protein and to vector sequences 3' to the gene. Additional nucleotides containing restriction sites to facilitate cloning were added to the 5' and 3' sequences respectively.

The 5' oligonucleotide primer had the sequence 5'-CAGGGAATTCTGAAGATGGCCAATTACACG-3'[SEQ ID NO:3] containing the underlined EcoRI restriction site, which encodes a start AUG, followed by 12 nucleotides of the human G-Protein Coupled Receptor HNFDS78 coding sequence set out in FIG. 1.

The 3' primer had the sequence 5'-GCATTTGGTGGATATCAGTTTACACTTCGG-3'[SEQ ID NO:4] containing the underlined EcoRI restriction site followed by 8 nucleotides.

The restrictions sites were convenient to restriction enzyme sites in the bacterial expression vectors pQE-9 which were used for bacterial expression in these examples. (Qiagen, Inc. Chatsworth, Calif. pQE-9 encodes ampicillin antibiotic resistance ("Ampr") and contains a bacterial origin of replication ("ori"), an IPTG inducible promoter, a ribosome binding site ("RBS"), a 6-His tag and restriction enzyme sites.

The amplified human G-Protein Coupled Receptor HNFDS78 DNA and the vector pQE-9 both were digested with EcoR1 and the digested DNAs then were ligated together. Insertion of the G-Protein Coupled Receptor HNFDS78 DNA into the EcoR1 restricted vector placed the G-Protein Coupled Receptor HNFDS78 coding region downstream of and operably linked to the vector's IPTG-inducible promoter and in-frame with an initiating AUG appropriately positioned for translation of G-Protein Coupled Receptor HNFDS78.

The ligation mixture was transformed into competent *E. coli* cells using standard procedures. Such procedures are described in Sambrook et al., *MOLECULAR CLONING: A LABORATORY MANUAL*, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan'"), was used in carrying out the illustrative example described here. This strain, which is only one of many that are suitable for expressing G-Protein Coupled Receptor HNFDS78, is available commercially from Qiagen.

Transformants were identified by their ability to grow on LB plates in the presence of ampicillin. Plasmid DNA was isolated from resistant colonies and the identity of the cloned DNA was confirmed by restriction analysis.

Clones containing the desired constructs were grown overnight ("O/N") in liquid culture in LB media supplemented with both ampicillin (100 ug/ml) and kanamycin (25 ug/ml).

The O/N culture was used to inoculate a large culture, at a dilution of approximately 1:100 to 1:250. The cells were grown to an optical density at 600 nm ("OD$^{600}$") of between 0.4 and 0.6. Isopropyl-B-D-thiogalactopyranoside ("IPTG") was then added to a final concentration of 1 mM to induce transcription from lac repressor sensitive promoters, by inactivating the lacI repressor. Cells subsequently were incubated further for 3 to 4 hours. Cells then were harvested by centrifugation and disrupted, by standard methods. Inclusion bodies were purified from the disrupted cells using routine collection techniques, and protein was solubilized from the inclusion bodies into 8M urea. The 8M urea solution containing the solubilized protein was passed over a PD-10 column in 2x phosphate buffered saline ("PBS"), thereby removing the urea, exchanging the buffer and refolding the protein. The protein was purified by a further step of chromatography to remove endotoxin. Then, it was sterile filtered. The sterile filtered protein preparation was stored in 2x PBS at a concentration of 95 micrograms per mL.

Example 2

Cloning and expression of human G-Protein Coupled Receptor HNFDS78 in a baculovirus expression system The cDNA sequence encoding the full length human G-Protein Coupled Receptor HNFDS78 protein, in the deposited clone is amplified using PCR oligonucleotide primers corresponding to the 5' and 3' sequences of the gene:

The 5' primer has the sequence 5'-CAGGGAATTCTGAAGATGGCCAATTACACG-3' [SEQ ID NO:3] containing the underlined EcoRI restriction enzyme site followed by 12 bases of the sequence of G-Protein Coupled Receptor HNFDS78 of FIG. 1 [SEQ ID NO:1]. Inserted into an expression vector, as described below, the 5' end of the amplified fragment encoding human G-Protein Coupled Receptor HNFDS78 provides an efficient signal peptide. An efficient signal for initiation of translation in eukaryotic cells, as described by Kozak, M., *J. Mol. Biol.* 196: 947–950 (1987) is appropriately located in the vector portion of the construct.

The 3' primer has the sequence 5'-GCATTTGGTGGATATCAGTTTACACTTCGG-3'[SEQ ID NO:4] containing the underlined EcoR1 restriction.

The amplified fragment is isolated from a 1% agarose gel using a commercially available kit ("Geneclean," BIO 101 Inc., La Jolla, Calif.). The fragment then is digested with BamH1 and Asp718 and again is purified on a 1% agarose gel. This fragment is designated herein F2.

The vector pRG1 is used to express the G-Protein Coupled Receptor HNFDS78 protein in the baculovirus expression system, using standard methods, such as those described in Summers et al, A MANUAL OF METHODS FOR BACULOVIRUS VECTORS AND INSECT CELL CULTURE PROCEDURES, Texas Agricultural Experimental Station Bulletin No. 1555 (1987). This expression vector contains the strong polyhedrin promoter of the Autographa californica nuclear polyhedrosis virus (AcMNPV) followed by convenient restriction sites. The signal peptide of AcMNPV gp67, including the N-terminal methionine, is located just upstream of a BamH1 site. The polyadenylation site of the simian virus 40 ("SV40") is used for efficient polyadenylation. For an easy selection of recombinant virus the beta-galactosidase gene from E. coli is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill in the art will readily appreciate, that construction provides appropriately located signals for transcription, translation, trafficking and the like, such as an in-frame AUG and a signal peptide, as required. Such vectors are described in Luckow et al., Virology 170: 31–39, among others.

The plasmid is digested with the restriction enzyme EcoR1 and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. E. coli HB 101 cells are transformed with ligation mix and spread on culture plates. Bacteria are identified that contain the plasmid with the human G-Protein Coupled Receptor HNFDS78 gene by digesting DNA from individual colonies using XbaI and BamHI and then analyzing the digestion product by gel electrophoresis. The sequence of the cloned fragment is confirmed by DNA sequencing. This plasmid is designated herein pBacG-Protein Coupled Receptor HNFDS78.

5 $\mu$g of the plasmid pBacG-Protein Coupled Receptor HNFDS78 is co-transfected with 1.0 $\mu$g of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). 1 $\mu$g of BaculoGold™ virus DNA and 5 $\mu$g of the plasmid pBacG-Protein Coupled Receptor HNFDS78 are mixed in a sterile well of a microtiter plate containing 50 $\mu$l of serum free Grace's medium (Life Technologies Inc., Gaithersburg, Md.). Afterwards 10 $\mu$l Lipofectin plus 90 $\mu$l Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 $\mu$l of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted G-Protein Coupled Receptor HNFDS78 is identified by DNA analysis including restriction mapping and sequencing. This is designated herein as V-G-Protein Coupled Receptor HNFDS78.

Sf9 cells are grown in Grace's medium supplemented with 10% heat-inactivated FBS. The cells are infected with the recombinant baculovirus V-G-Protein Coupled Receptor HNFDS78 at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 $\mu$Ci of 35S-methionine and 5 $\mu$Ci 35S cysteine (available from Amersham) are added. The cells are further incubated for 16 hours and then they are harvested by centrifugation, lysed and the labeled proteins are visualized by SDS-PAGE and autoradiography.

Example 3

Expression of G-Protein Coupled Receptor HNFDS78 in COS cells

The expression plasmid, G-Protein Coupled Receptor HNFDS78 HA, is made by cloning a cDNA encoding G-Protein Coupled Receptor HNFDS78 into the expression vector pcDNAI/Amp (which can be obtained from Invitrogen, Inc.).

The expression vector pcDNAI/amp contains: (1) an E. coli origin of replication effective for propagation in E. coli and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire G-Protein Coupled Receptor HNFDS78 precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., Cell 37: 767 (1984). The fusion of the HA tag to the target protein allows easy detection of the recombinant protein with an antibody that recognizes the HA epitope.

The plasmid construction strategy is as follows.

The G-Protein Coupled Receptor HNFDS78 cDNA of the deposit clone is amplified using primers that contained convenient restriction sites, much as described above regarding the construction of expression vectors for expression of G-Protein Coupled Receptor HNFDS78 in E. coli and S. fugiperda.

To facilitate detection, purification and characterization of the expressed G-Protein Coupled Receptor HNFDS78, one of the primers contains a hemagglutinin tag ("HA tag") as described above.

Suitable primers include that following, which are used in this example.

The 5' primer, containing the underlined EcoR1 site has the following sequence 5'-CAGGGAATTCTGAAGATGGCCAATTACACG-3' [SEQ ID NO:3].

The 3' primer, containing the underlined EcoR1 has the following sequence; 5'-GCATTTGGTGGATATCAGTTTACACTTCGG-3'[SEQ ID NO:4].

The PCR amplified DNA fragment and the vector, pcDNAI/Amp, are digested with and then ligated. The ligation mixture is transformed into E. coli strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolated from resistant colonies and examined by restriction analysis and gel sizing for the presence of the G-Protein Coupled Receptor HNFDS78-encoding fragment.

For expression of recombinant G-Protein Coupled Receptor HNFDS78, COS cells are transfected with an expression vector, as described above, using DEAE-DEXTRAN, as described, for instance, in Sambrook et al., *MOLECULAR CLONING: A LABORATORY MANUAL*, Cold Spring Laboratory Press, Cold Spring Harbor, N.Y. (1989).

Cells are incubated under conditions for expression of G-Protein Coupled Receptor HNFDS78 by the vector.

Expression of the G-Protein Coupled Receptor HNFDS78 HA fusion protein is detected by radiolabelling and immunoprecipitation, using methods described in, for example Harlow et al., *ANTIBODIES: A LABORATORY MANUAL*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 0.1% SDS, 1% NP40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 4

Gene therapeutic expression of human G-Protein Coupled Receptor HNFDS78

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

G-Protein Coupled Receptor HNFDS78 cDNA capable of expressing active G-Protein Coupled Receptor HNFDS78, is isolated. The ends of the fragment are modified, if necessary, for cloning into the vector. For instance, 5' overhanging may be treated with DNA polymerase to create blunt ends. 3' overhanging ends may be removed using S1 nuclease. Linkers may be ligated to blunt ends with T4 DNA ligase.

Equal quantities of the Moloney murine leukemia virus linear backbone and the G-Protein Coupled Receptor HNFDS78 fragment are mixed together and joined using T4 DNA ligase. The ligation mixture is used to transform E. coli and the bacteria are then plated onto agar-containing kanamycin. Kan$^r$ phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the G-Protein Coupled Receptor HNFDS78 gene is introduced into the packaging cells by standard techniques. Infectious viral particles containing the G-Protein Coupled Receptor HNFDS78 gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce G-Protein Coupled Receptor HNFDS78 product, and the biological actions of the protein are conveyed to the host.

It will be clear that the invention may be practiced otherwise than as particularly described in the foregoing description and examples.

Numerous modifications and variations of the present invention are possible in light of the above teachings and, therefore, are within the scope of the appended claims.

Example 5

Transient expression of receptor in mammalian cell lines

In order to maximize receptor expression, 5' and 3' untranslated regions (UTRs) were removed from the receptor cDNA (SEQ ID NO:3) prior to insertion into a pCDN expression vector (Aiyar, N., et al., Molecular and Cellular Biochemistry 131:75–86 (1994)). Since PCR was used to trim the cDNA, the DNA sequences were routinely confirmed by routine sequencing methods prior to expression.

Initially transient transfection of G-Protein Coupled Receptor HNFDS78 in COS cells was performed using the dextran sulfate method. Briefly, 1×10$^7$ COS cells were grown in 245×245-mm tissue culture plates for 24 hours to 50–70% confluency. The cells were washed with PBS and then transfected with 100 µg of G-Protein Coupled Receptor HNFDS78 cDNA in CMEM media containing 10% Neuserum 1% glutamine, DE dextran and chloroquine media and incubated for 3 hours. The cells were then shocked with 10% DMSO, washed and incubated for three days in DMEM medium containing 10% fetal bovine serum, 1% glutamine.

Example 6

Ligand binding studies with receptor

G-Protein Coupled Receptor HNFDS78 was transiently expressed in COS cells as described above. Membranes were prepared and binding studies initiated using iodinated MCP-1 (Cambadiere, C., et al., P.M.J. Biol. Chem. 270: 16491 (1995), MCP-3 (Cambadiere, C., et al., P.M.J. Biol. Chem. 270: 16491 (1995), MCP-4 (WO-US94/05384) and chemokine CKβ-8. Methods useful for isolating CKβ-8 are disclosed in US94/07256 and U.S. Pat. No. 5,504,003. CKβ-8 amino acid sequence [SEQ ID NO:6] and nucleotide sequence [SEQ ID NO:5] are set forth in FIG. 2. For positive controls, membranes were used from the CHO-CC-CKR-2B receptor (Cambadiere, C., et al., P.M.J. Biol. Chem. 270: 16491 (1995)) and differentiated EOL-3 cells. Results of these studies are presented in Table 1 below.

TABLE 1

| | Binding Analysis | | | |
|---|---|---|---|---|
| Receptor | MCP-1 | MCP-3 | MCP-4 | CKβ-8 |
| G-Protein Coupled Receptor HNFDS78 | | | | + |
| CKR-2B | +++ | | ++ | |
| EOL-3 | ++ | +++ | ++ | |

The G-Protein Coupled Receptor HNFDS78 showed specific binding with chemokine CKβ-8. Thus, CKβ-8 is a ligand of G-Protein Coupled Receptor HNFDS78.

Example 7 mRNA expression in Different Cell Types

Poly A+RNA was isolated from various cell types using the well known guanidium thiocyanate acid-phenol method followed by isolation using oligo dT column. RNA dot blot analysis was performed with a template manifold apparatus (Scheicher & Schuell, Keene, N.H.) to assure uniform dot size. Poly A+RNA was applied using 0.5 μg of RNA. The RNA samples were denatured by adjusting them to 1M formaldehyde and heating them to 550° C. for 15 minutes. The samples were diluted into 20 volumes of 3 M NaCl containing 0.3 M trisodium citrate and applied to nitrocellulose filters under a gentle vacuum. The filters were washed with additional diluted, baked at 80° C. for 2hours and then hybridized under high stringency in 50% formamide, 5×SSPE, 5×Denhardt's reagent, 0.1% SDS, and 100 μg/ml yeast tRNA. The blots were washed with 0.1×SSC, 0.1% SDS at 50° C. and exposed to X-ray film for 48 hours at −70° C. Quanitation of the dots were performed using Phospho-Imaging analysis and data in relative optical density units (OD Units) was determined. The data below in Table 2 show clearly that G-Protein Coupled Receptor HNFDS78 is expressed in monocytes and is unpregulated if form cells.

TABLE 2

| mRNA Expression in Different Cell Types | |
|---|---|
| Cell Type | OD Units |
| Monocytes | 4.6 |
| Macrophages | 41.8 |
| Foam Cells | 80.2 |
| MonoMac | 1.1 |
| THP-1 | 6.4 |
| PBL | 11.6 |
| EOL3 Cells | 2.6 |
| Neutrophil | 0.9 |
| T-Cells | 2.3 |
| SM Cells | 1.07 |
| Endothelial Cells | 2.6 |
| Yeast RNA (negative control) | 0.0 |

What is claimed is:

1. An isolated polynucleotide comprising a nucleotide sequence encoding a polypeptide comprising amino acids 1 to 344 of SEQ ID NO:2.

2. The polynucleotide of claim 1 wherein the polynucleotide is DNA.

3. The polynucleotide of claim 1 wherein the polynucleotide is RNA.

4. The polynucleotide of claim 2 comprising nucleotide sequence set forth in SEQ ID NO:1 that encodes amino acids 1 to 344 of SEQ ID NO:2.

5. The polynucleotide of claim 2 which encodes a polypeptide comprising amino acids 21 to 344 of SEQ ID NO:2.

6. A vector comprising the DNA of claim 2.

7. A host cell comprising the vector of claim 6.

8. A process for producing a polypeptide comprising: expressing from the host cell of claim 7 a polypeptide encoded by said DNA.

9. A process for producing a cell which expresses a polypeptide comprising transforming or transfecting the cell with the vector of claim 6 such that the cell expresses the polypeptide encoded by the DNA contained in the vector.

10. The polynucleotide comprising nucleotides 1 to 1050 set forth in SEQ ID NO:1.

11. A polynucleotide sequence of claim 10 which is DNA.

12. An isolated polynucleotide comprising a poynucleotide encoding the same mature polypeptide expressed by the human cDNA contained in ATCC Deposit No. 98099.

13. A polynucleotide sequence which is fully complementary to any of the isolated polynucleotides in any one of claims 1–5, 10 or 12.

* * * * *